United States Patent [19]

Strubé

[11] 4,169,462
[45] Oct. 2, 1979

[54] CRIB DEATH DETECTOR

[76] Inventor: Richard E. Strubé, 3 Meadowood Ct., Bradford, Pa. 16701

[21] Appl. No.: 798,452

[22] Filed: May 19, 1977

[51] Int. Cl.² .............................................. A61B 5/08
[52] U.S. Cl. .......................................................128/721
[58] Field of Search ................ 128/2 R, 2 S, DIG. 29

[56] References Cited

U.S. PATENT DOCUMENTS

| | | | |
|---|---|---|---|
| 3,545,429 | 12/1970 | Pelta et al. | 128/DIG. 29 X |
| 3,584,618 | 6/1971 | Reinhard | 128/DIG. 29 X |
| 3,608,542 | 9/1971 | Pacela et al. | 128/DIG. 29 X |
| 3,643,652 | 2/1972 | Beltram | 128/DIG. 29 X |
| 3,727,606 | 4/1973 | Sielaff | 128/DIG. 29 X |
| 3,730,173 | 5/1973 | Deaton | 128/DIG. 29 X |
| 3,782,368 | 1/1974 | Riebold | 128/DIG. 29 X |
| 3,802,417 | 4/1974 | Lang | 128/DIG. 29 X |
| 3,898,981 | 8/1975 | Basham | 128/DIG. 29 X |

FOREIGN PATENT DOCUMENTS 1398752  6/1975  United Kingdom ........ 128/DIG. 29 X

OTHER PUBLICATIONS

"Respiration Monitor With Automatic Stimulation for Premature and Newborn Babies," Fresenius Corp., West Germany, Feb. 1974.

Chess, G. F. et al., "Apnea Monitor for Laboratory Animals," Med. & Biol. Engr., v. 14, #1, pp. 97-100, Jan. 1976.

*Primary Examiner*—Robert W. Michell
*Assistant Examiner*—Francis J. Jaworski

[57] ABSTRACT

The motion detector described in this disclosure is an apparatus for monitoring the minute movements made by the body during the process of breathing. This is accomplished by converting the body movements into electrical signals with an adapted piezoelectric transducer. This electrical signal is used to restart a counting circuit which uses a variable free running Schmitt-trigger oscillator signal for counting. The output of the counting circuit is connected to an audio alarm through a switch. This switch also connects the Schmitt-trigger oscillator to the audio alarm when the low voltage detector circuit indicates that the supply voltage has dropped below a predetermined level.

3 Claims, 1 Drawing Figure

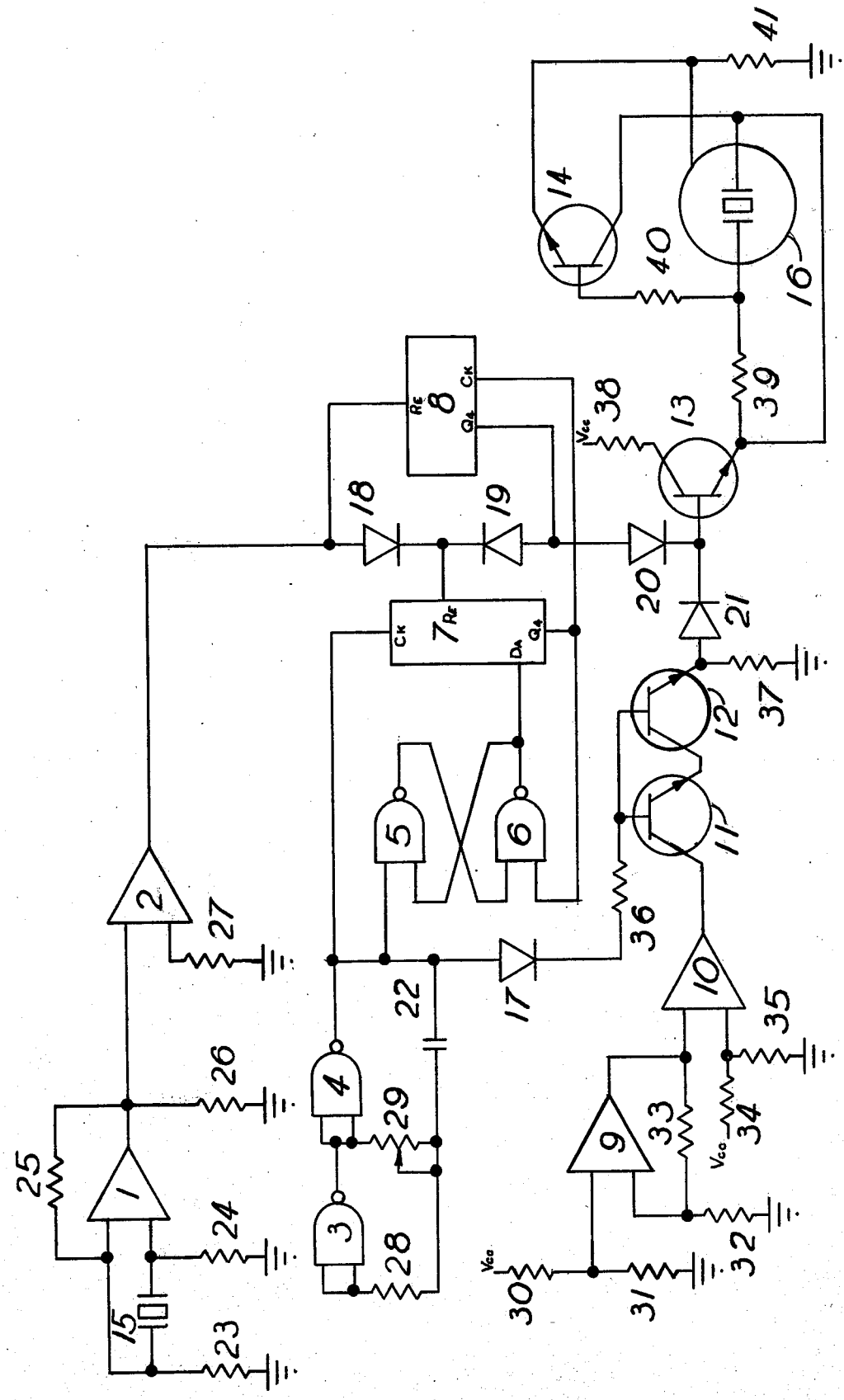

CRIB DEATH DETECTOR

BACKGROUND OF THE INVENTION

The problem of sudden unexpected death among children, especially infants, is unfortunately not a new phenomena and causes of these deaths are neither known nor are they fully understood. Fortunately though, there is a period of time between apparent death and permanent death during which if failure of respiration can be detected, there remains enough time left to save the life.

The prior art presents a number of devices which can detect this pre-death situation. Typically though, these devices require either elaborate procedures, or controlled environments, or facility power, as in U.S. Pat. Nos. 3,643,652 "Medical Breathing Measuring System" by Delfin J. Beltran, or 3,730,173 "Stimulation Method and Apparatus for Attempting to Return a Physiological Parameter of a Patient to Normal" by David W. Deaton, or 3,898,981 "Respiration Monitoring Apparatus" by Raymon B. Basham, or 3,545,429 "Respiration Monitor" by Edmond R. Pelta, and others.

SUMMARY OF THE INVENTION

Because the apparatus is designed to be attached to an infant, this requires that everything associated with the project be miniaturized. Therefore, the design criteria used was that the detector must be: (A) small enough to be attached to an infant; (B) contain its own power source; and (C) not be overly affected by the moisture found around infants.

To incorporate these criteria, the project broke into four (4) major areas: (A) a self contained power source; (B) an audio warning device; (C) a logic or computional package, and (D) an electro-mechanical transducer.

BRIEF DESCRIPTION OF THE DRAWING

FIG. 1 is a schematic diagram of the motion detector monitoring system in accordance with the invention.

DETAILED DESCRIPTION OF THE INVENTION

Nand gates 3 and 4 along with their associated circuitry 22, 28, 29 form a variable free running Schmitt-trigger oscillator. This oscillator is used as the input to the counter circuit formed by nand gates 5 and 6 along with shift registers 7 and 8, plus their associated circuitry 18 and 19.

The counter circuit is reset with an impulse derived from mechanical pressure, the result of breathing, on the piezoceramic crystal 15. The impulse from the piezoceramic crystal is properly shaped and level translated by amplifiers 1 and 2, plus their associated circuitry 23, 24, 25, 26, 27.

If the counter circuit completes the count, a transistor switch 13 and associated circuitry 38 is energized through a diode 20. When the transistor switch is energized a warning tone is emitted by the vibrating crystal resonator 16 and its associated circuitry 14, 39, 40, 41 signifying that breathing has stopped.

Other amplifiers 9 and 10 along with their associated circuitry 30, 31, 32, 33, 34, 35 form a switch which will detect when the power pack is getting low in power. When this happens, a signal from this low power detector is combined with the output from the Schmitt-trigger oscillator via switching transistors 11 and 12, plus their associated circuitry 17, 36, 37, 21 resulting in a pulsating signal level through diode 21 to the switching transistor 13. The outcome of this is a pulsating tone emitted from the crystal resonator 16 signaling that the power pack should be charged.

What is claimed is:

1. A portable motion detector for monitoring the respirational activity of a patient, which comprises; piezoelectric transducer means adapted for converting body expansion during the breathing process into electrical signals, counting circuit coupled to the output of said transducer means for producing an output signal representative of the absence of a breathing signal over a predetermined counting period, an oscillator circuit coupled to the input of said counting circuit for providing a signal for counting, an audio output means coupled to the output of said counting circuit for producing a tone signal indicating that respiration has ceased, low voltage detector circuit means coupled to the input of said audio output means for producing an output indicative of supply voltage dropping below a predetermined level, switch means coupled to the output of said oscillator circuit and to the output of said low voltage detection circuit means for enabling output of said low voltage detection circuit means whereby a pulsating tone signal indicative of a low battery power is produced.

2. An apparatus as in claim one (1) the said oscillator is a Schmitt-trigger oscillator.

3. An apparatus as in claim one (1) the said oscillator is a variable oscillator.

* * * * *